(12) United States Patent
Musicki et al.

(10) Patent No.: US 9,120,772 B2
(45) Date of Patent: Sep. 1, 2015

(54) DISUBSTITUTED 3,4-DIAMINO-3-CYCLOBUTENE-1,2-DIONE COMPOUNDS FOR USE IN THE TREATMENT OF CHEMOKINE-MEDIATED DISEASES

(71) Applicant: Galderma Research & Development, Biot (FR)

(72) Inventors: Branislav Musicki, Nice (FR); Jerôme Aubert, Grasse (FR); Patricia Rossio, Grasse (FR); Marlène Schuppli-Nollet, Le Bar sur Loup (FR); Laurence Clary, La Colle-sur-Loup (FR); Jean-Guy Boiteau, Valbonne (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/354,537

(22) PCT Filed: Oct. 26, 2012

(86) PCT No.: PCT/FR2012/052476
§ 371 (c)(1),
(2) Date: Apr. 25, 2014

(87) PCT Pub. No.: WO2013/061002
PCT Pub. Date: May 2, 2013

(65) Prior Publication Data
US 2015/0087675 A1       Mar. 26, 2015

Related U.S. Application Data

(60) Provisional application No. 61/552,826, filed on Oct. 28, 2011.

(30) Foreign Application Priority Data

Oct. 28, 2011   (FR) ...................................... 11 59831

(51) Int. Cl.
C07D 409/06     (2006.01)
C07D 407/06     (2006.01)
C07D 405/06     (2006.01)

(52) U.S. Cl.
CPC ............ *C07D 409/06* (2013.01); *C07D 405/06* (2013.01); *C07D 407/06* (2013.01)

(58) Field of Classification Search
None
See application file for complete search history.

(56) References Cited

FOREIGN PATENT DOCUMENTS

WO    2004/011418 A1    2/2004

OTHER PUBLICATIONS

International Search Report dated Dec. 19, 2012 corresponding to International Patent Application No. PCT/FR2012/052476, 2 pages.

*Primary Examiner* — Timothy R Rozof
(74) *Attorney, Agent, or Firm* — Dentons US LLP

(57) ABSTRACT

Disubstituted 3,4-diamino-3-cyclobutene-1,2-dione compounds corresponding to general formula (I) are disclosed. Also disclosed, are pharmaceutical compositions including these compounds and methods of using these compounds and compositions for the treatment of chemokine-mediated diseases.

6 Claims, 5 Drawing Sheets

Scheme 1

DISUBSTITUTED 3,4-DIAMINO-3-CYCLOBUTENE-1,2-DIONE COMPOUNDS FOR USE IN THE TREATMENT OF CHEMOKINE-MEDIATED DISEASES

CROSS-REFERENCE TO PRIOR APPLICATIONS

This application is a National Stage of PCT/FR2012/052476, filed Oct. 26, 2012, and designating the United States (published in English on May 2, 2013, as WO 2013/061002 A1), which claims priority under 35 U.S.C. §119 to U.S. Provisional Patent Application No. 61/552,826, filed Oct. 28, 2011, and French Patent Application No. 1159831, filed Oct. 28, 2011 each hereby expressly incorporated by reference in its entirety and each assigned to the assignee hereof.

FIELD OF THE INVENTION

The present invention relates to novel disubstituted 3,4-diamino-3-cyclobutene-1,2-dione compounds, to the pharmaceutical compositions containing these compounds and also to the use of these compounds and of these compositions for the treatment of chemokine-mediated diseases.

STATE OF THE ART PRIOR TO THE INVENTION

Chemokines or cytokines are small soluble proteins. Their most well-known role is the attraction of immune system cells and the control of the activation state of said cells. All chemokines perform their functions by binding to G protein-coupled receptors. Some chemokines are considered to be pro-inflammatory. The secretion of these chemokines can be induced during the immune response in order to promote the arrival of immune system cells at an infectious site.

There are two types of chemokines: pro-inflammatory chemokines and constitutive chemokines.

The pro-inflammatory (or "inducible") chemokines are produced at sites of inflammation by tissue cells or leukocytes that have infiltrated, after contact with a pathogenic agent.

The constitutive (or "homeostatic") chemokines are produced in the lymphoid organs and in certain non-lymphoid organs such as the skin and mucous membranes. They regulate lymphocyte trafficking and the localization of lymphocytes within these organs during lymphopoiesis, but also for maintaining immunosurveillance.

The nomenclature of these chemokine receptors is based on the group of chemokines to which its ligand belongs. Thus, the receptors corresponding to the chemokines of the CXC group are, for example, called CXCR1, CXCR2, CXCR3, CXCR4, etc., and the receptors corresponding to the chemokines of the CC group are, for example, called CCR1, CCR2, CCR3, etc. These receptors all have a similar tertiary structure, and they are coupled to a G protein: they are therefore part of the GPCR (G Protein-Coupled Receptor) superfamily.

Interleukin-8 or IL-8 (also known as CXCL-8) is a member of the CXC chemokine family, which plays an essential role in the recruitment of neutrophils to the inflammation site. Two receptors, CXCR1 and CXCR2, are known to be specifically activated by IL-8. While CXCR2 binds with strong affinity to IL-8 and to the related chemokines, such as CXCL6, CXCL5, CXCL3, CXCL2 and CXCL1, CXCR1 binds only to IL-8. High levels of IL-8 and of related chemokines (CXCL5, CXCL2 & CXCL1) have been described in the lesions of inflammatory acne (J Invest Dermatol. 2006; 126:1071-9; Am J Pathol. 2005; 166(6):1691-9; Diagn Pathol. 2007 Jan. 30; 2:4).

First indications demonstrate the expression of CXCR2 in inflammatory acne (Trivedi et al. J Invest Dermatol. 2006 126(5):1071-9). Thus, double antagonists of CXCR1 and CXCR2 might make it possible to rapidly reduce the harmful effects of the IL-8-mediated inflammatory response.

Patent application WO 02/083624 (Schering/Pharmacopeia) discloses more particularly substituted 1,2-cyclobutenedione compounds capable of modulating the activity of CXC-type chemokine receptors, and more particularly the activity of the CXCR1 and CXCR2 receptors. Among these compounds, the compound SCH-527123 (corresponding to example 360.71 on page 281), also called Navarixin, is in the process of being developed (Phase II) for the treatment of chronic obstructive pulmonary disease (or COPD). This compound has also been the subject of phase II studies in asthma and in psoriasis, but these developments have been stopped.

It is currently known that many pathologies of inflammatory type are mediated by chemokines. However, there is a need, which has not been satisfied to date, to treat the inflammatory component of the pathologies of interest in the dermatology field, for instance acne, rosacea or alternatively neutrophilic dermatosis, in particular psoriasis.

Likewise, the promise of obtaining effective new therapies for treating chemokine-mediated diseases using chemokine receptor antagonists has not been fulfilled. Indeed, several clinical studies have failed in phase II. One of the reasons which may explain these failures is the overlap of the biological effects of the various chemokines induced in a pathological situation. To date, the objective of the standard drug discovery process is to identify molecules which target a specific receptor without an off target effect. This approach is without doubt not the most suitable for treating complex inflammatory diseases. An increasing number of approaches appear to favor the search for antagonist molecules with a broad spectrum of action (promiscuous compounds), said approaches possibly thus proving to be more effective in treating complex and multifactorial diseases (Frantz S. Drug discovery: playing dirty. Nature. 2005 Oct. 13; 437(7061):942-3; Roth B L, Sheffler D J, Kroeze W K. Magic shotguns versus magic bullets: selectively non-selective drugs for mood disorders and schizophrenia. Nat Rev Drug Discov. 2004 April; 3(4): 353-9).

As it happens, the applicant has discovered novel compounds which not only have an antagonist activity with respect to receptors of CXCR1 and CXCR2 type, but also a strong antagonist activity with respect to chemokine receptors, in particular CCR6 and CXCR3 receptors. These novel compounds surprisingly exhibit a polypharmacology, which makes them of additional interest compared with the already known compounds in the treatment of chemokine-mediated pathologies, and more particularly pathologies of dermatological type. Furthermore, these novel compounds exhibit a hepatic stability which is much lower than that of the already described compounds capable of blocking the activation of CXCR1 and CXCR2 receptors, for instance the SCH-527123 compound. This particular property provides the advantage of having novel compounds which, surprisingly, have a profile that is more suitable for the topical treatment of pathologies of dermatological type. Indeed, their hepatic instability leads to low, or even zero, systemic exposure, and therefore limited side effects. Another particularity of the compounds described in the present invention is their dissociation constant with respect to receptors of CXCR1 and CXCR2 type, said constant being much lower than that of the compounds described in the patent application WO 02/083624, for instance SCH-527123. Indeed, the SCH-527123 molecule has been described as having a dissociation time of about 22 h (pseudo-irreversible dissociation) (Pharmacological Characterization of SCH-527123, a Potent Allosteric CXCR1/CXCR2 Antagonist. JPET 322:477-485, 2007), whereas the dissociation times of the compounds of the present invention are much shorter.

Examples in the literature show that rapid dissociation of antagonists promotes a decrease in their toxicity. This has been described for the antagonists of dopamine D2 receptors (*Am J Psychiatry* (2001) 158(3):360-369), and of N-methyl-D-aspartate (NMDA) receptors (*Nat Rev Drug Disc* (2006) 5(2):160-170) and also for nonsteroidal anti-inflammatory drugs (*Lett Drug Des Discov* (2006) 3(8):569-574 and *Pharm Med* (2008) 22(1):23-34). Indeed, a long dissociation time would have a tendency to induce adverse effects. With rapid dissociation times, the compounds according to the invention consequently exhibit reduced side effects.

SUMMARY OF THE INVENTION

A first subject according to the invention relates to novel disubstituted 3,4-diamino-3-cyclobutene-1,2-dione compounds corresponding to general formula (I) below:

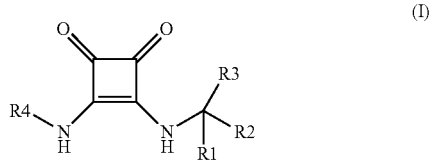

(I)

and also the pharmaceutically acceptable salts, solvates or hydrates thereof, for which the substituents R1, R2, R3 and R4 are as defined hereinafter in the detailed description of the invention.

A second subject according to the invention relates to a pharmaceutical composition comprising an effective amount of a compound corresponding to general formula (I), or of one of the pharmaceutically acceptable salts thereof or one of the pharmaceutically acceptable solvates or hydrates thereof, in combination with a pharmaceutically acceptable solvent or support.

A third subject according to the invention relates to a compound or a pharmaceutical composition as described above, for use as a medicament.

A fourth subject according to the invention relates to a compound or a pharmaceutical composition as described above, for use in the treatment of chemokine-mediated diseases.

A fifth subject according to the invention relates to a compound or pharmaceutical composition as described above, for use in the treatment of diseases of the group comprising neutrophilic dermatosis, and in particular psoriasis, atopic dermatitis, acne, rosacea, asthma, chronic obstructive pulmonary diseases, respiratory diseases in adults, arthritis, inflammatory bowel diseases, Crohn's disease, transplant rejection, cystic fibrosis and skin cancers.

DETAILED DESCRIPTION OF THE INVENTION

Figure 1:
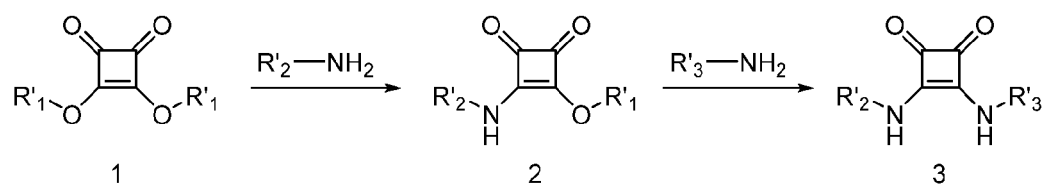
FIG. 1 depicts Scheme 1, a synthesis of the compounds of formula (III).
Figure 2:
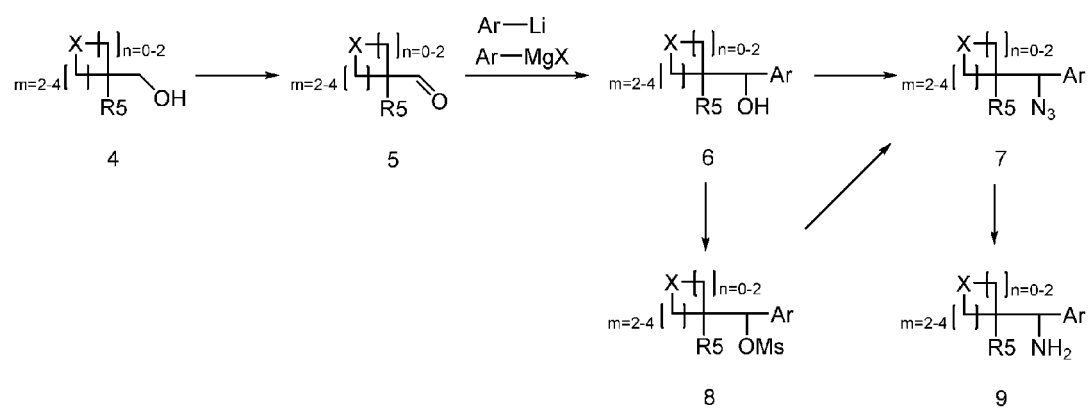
FIG. 2 depicts Scheme 2, a synthesis of amines of formula (IX) from reagents.
Figure 3:
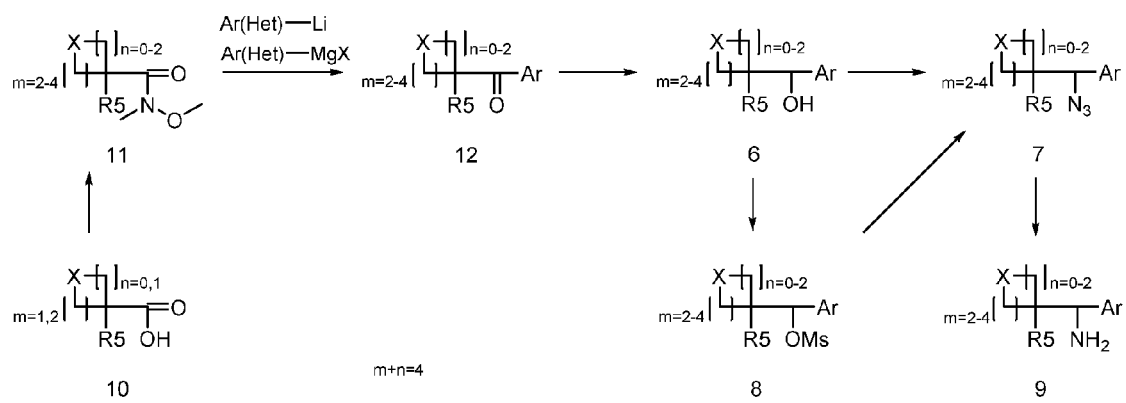
FIG. 3 depicts Scheme 3, an alternative synthesis of amines of formula (IX) from acids (X).
Figure 4:
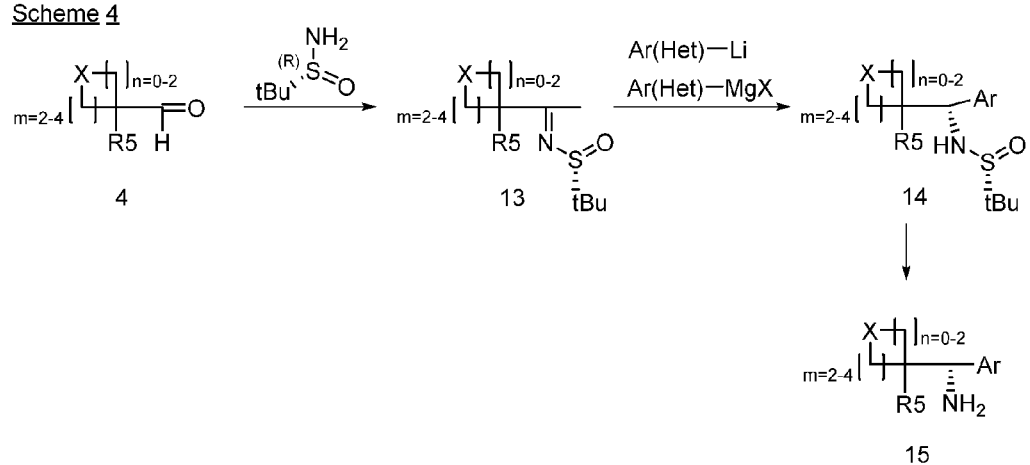
FIG. 4 depicts Scheme 4, a preparation of a chiral primary amine R'3-NH$_2$ having structure (XV) by the condensation of enantiomerically pure 2-methyl-2-propanesulfinamide (tert-butanesulfinamide).
Figure 5:
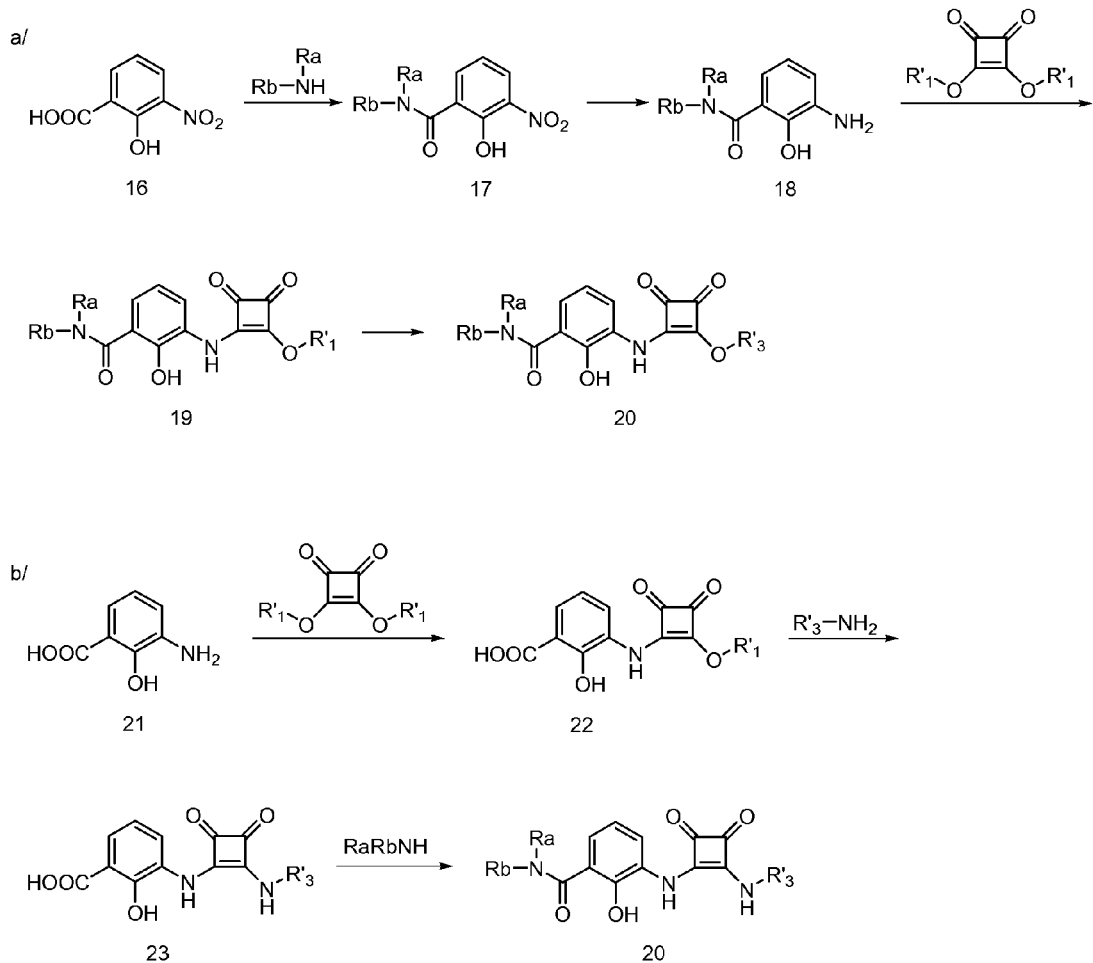
FIG. 5*a*/ depicts Scheme 5a, a preparation of the amide derivatives of 3-aminosalicylic acid of formula (XVIII) from 3-nitrosalicyclic acid (XVI).
FIG. 5*b*/ depicts Scheme 5b, a preparation of compound (XXIII) form the coupling of 3-aminosalicylic acid (XXI) with dimethyl or diethyl squarate.

Unless otherwise indicated, the following definitions apply to the entire description and claims.

These definitions apply independently of whether a term is used alone or in combination with other terms. Thus, for example, the definition of the term "aryl" applies both to "aryl" as such and to the "aryl" part of the term "aryloxy".

"Alkyl" denotes a linear or branched, saturated hydrocarbon-based chain of which the number of carbon atoms is specified.

When the number of carbon atoms is not specified, this means that the alkyl chain contains from 1 to 20 carbon atoms.

The preferred alkyl radicals contain from 1 to 12 carbon atoms, and those which are even more preferred contain from 1 to 6 carbon atoms in the chain.

"Alkoxy" denotes an oxygen substituted with an alkyl radical as previously defined.

Examples of alkoxy radicals include methoxy, ethoxy, n-propoxy, isopropoxy and n-butoxy radicals.

"Aryl" denotes a monocyclic or polycyclic (2 to 3 rings) aromatic cyclic system comprising from 6 to 14 carbon atoms, and preferably from 6 to 10 carbon atoms.

By way of examples of aryl radicals, mention may be made of phenyl, naphthyl, indenyl, tetrahydronaphthyl, indanyl, anthracenyl and fluorenyl groups.

"Heteroaryl" denotes a monocyclic or polycyclic (2 to 3 rings) aromatic system comprising from 5 to 14 cyclic atoms, preferably from 5 to 10 cyclic atoms, in which one or more of the cyclic atoms represent(s) one or more (1 to 5) heteroatom(s) chosen from the group comprising nitrogen, oxygen and sulfur.

The preferred heteroaryls contain 5 or 6 cyclic atoms and 1 to 3 heteroatoms.

The prefix aza, oxa or thia before the name of the heteroaryl root signifies that at least one nitrogen, one oxygen or one sulfur is respectively present in the ring.

A nitrogen atom of a heteroaryl can be optionally oxidized to N-oxide.

By way of examples of appropriate heteroaryls, mention should be made of the following heteroaryls:

pyridyl, pyrazinyl, furanyl, thienyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4 triazinyl and benzothiazolyl.

"Arylalkyl" denotes a radical of which the aryl and alkyl parts are as defined above.

By way of examples of arylalkyl, mention may be made of benzyl, phenethyl and naphthalenylmethyl radicals.

The linkage to the structure to which it is attached is via the alkyl radical.

"Heteroarylalkyl" denotes a radical of which the heteroaryl and alkyl parts are as defined above.

By way of examples of heteroarylalkyl, mention may be made of pyridylmethyl, pyridylethyl, imidazolylmethyl, imidazolylethyl, pyrazolylmethyl and pyrazolylethyl groups.

The linkage to the structure to which it is attached is via the alkyl radical.

"Cycloalkyl" denotes a nonaromatic hydrocarbon-based cyclic system, having from 3 to carbon atoms, preferably from 5 to 10 carbon atoms, and from one to three rings.

The preferred cycloalkyl radicals contain from 5 to 7 cyclic atoms.

By way of examples of cycloalkyl radicals, mention may be made of cyclopropyl, cyclopentyl, cyclohexyl, cycloheptyl, norbornyl and adamantyl radicals.

"Cycloalkylalkyl" denotes a radical of which the cycloalkyl and alkyl parts are as defined above.

By way of examples of cycloalkylalkyl, mention may be made of cyclopropylmethyl, cyclopropylethyl, cyclobutylmethyl, cyclobutylethyl, cyclopentylmethyl, cyclopentylethyl, cyclohexylmethyl, cyclohexylethyl, norbornylmethyl and adamantylmethyl groups.

The linkage to the structure to which it is attached is via the alkyl radical.

"Heterocycloalkyl" denotes a nonaromatic hydrocarbon-based cyclic system, having from 4 to 10 carbon atoms, preferably from 5 to 10 carbon atoms, and from one to three rings, and comprising from one to three heteroatoms chosen from the group consisting of nitrogen, oxygen and sulfur.

The preferred heterocycloalkyl radicals contain from 5 to 7 cyclic atoms.

By way of examples of heterocycloalkyl radicals, mention should be made of tetrahydrofuranyl, tetrahydrothiophenyl, tetrahydropyranyl and 7-oxabicyclo[2.2.1]heptanyl radicals.

"Fluoroalkyl" denotes an alkyl radical as previously defined, substituted with one or more fluorine atoms.

By way of examples of fluoroalkyl radicals, mention may be made of fluoromethyl, difluoromethyl, 2-fluoroethyl, 2,2-difluoroethyl and 2,2,2-trifluoroethyl radicals.

"Perfluoroalkyl" denotes an alkyl radical as previously defined, in which each hydrogen atom has been substituted with a fluorine atom.

By way of examples of perfluoro radicals, mention may be made of trifluoromethyl and pentafluoroethyl radicals.

Thus, a first subject according to the invention relates to novel disubstituted 3,4-diamino-3-cyclobutene-1,2-dione compounds corresponding to general formula (I) below, or one of the pharmaceutically acceptable salts or solvates thereof:

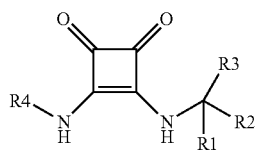
(I)

in which,

R1 represents a hydrogen atom or a methyl,

R2 represents a six-membered ring chosen from the structures (1) to (7) below:

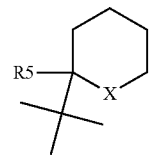
(1)

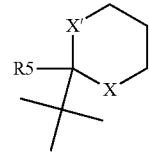
(2)

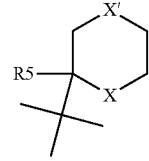
(3)

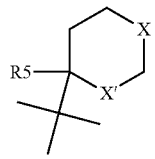
(4)

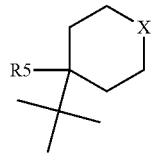
(5)

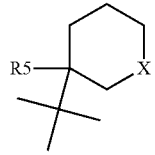
(6)

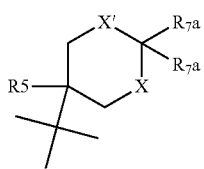
(7)

in which R5, X, X' and R7a have the meaning given hereinafter,

R3 represents an aromatic or heteroaromatic ring selected from the group consisting of the rings corresponding to formulae (a) to (o) below:

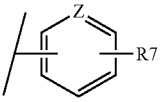
(a)

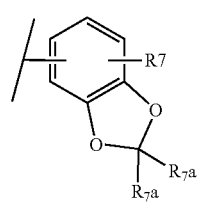
(b)

US 9,120,772 B2

7
-continued (c) 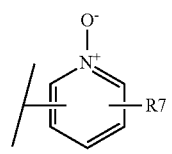

(d) 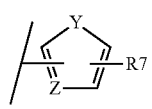

(e) 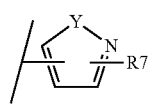

(f) 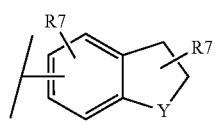

(g) 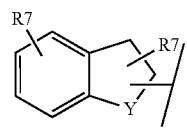

(h) 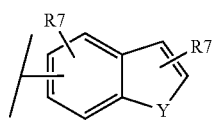

(i) 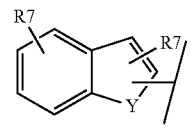

(j) 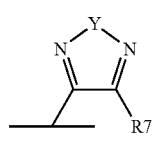

(k) 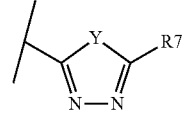

(l) 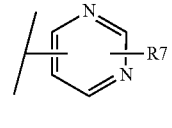

(m) 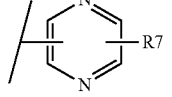

(n) 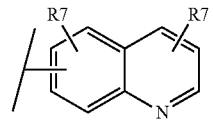

8
-continued (o) 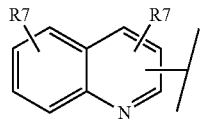

in which R7, R7a, Y and Z have the meaning given hereinafter, it being specified that the rings (a) to (o) can optionally bear several R7 groups, which may be identical or different, the total number of such R7 groups being at most equal to the number of substitutable atoms of the ring;

R4 represents an aromatic or heteroaromatic ring selected from the group consisting of the rings corresponding to formulae (p) to (z) and (aa) to (ak) below:

(p) 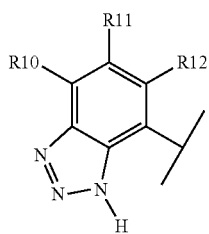

(q) 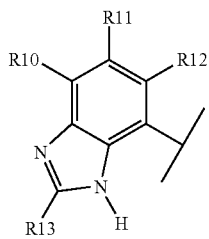

(r) 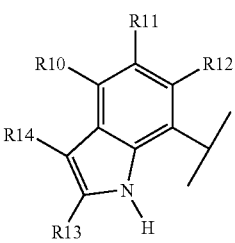

(s) 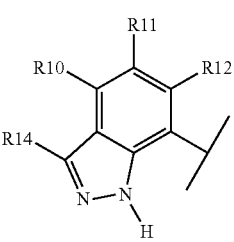

(t) 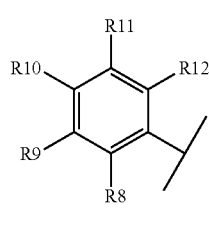

-continued
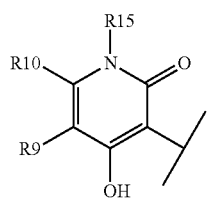 (u)
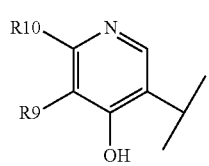 (v)
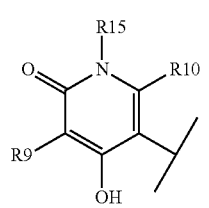 (w)
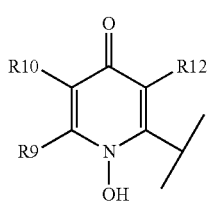 (x)
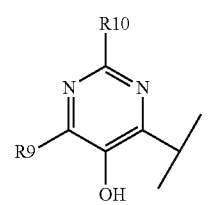 (y)
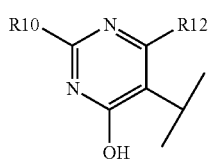 (z)
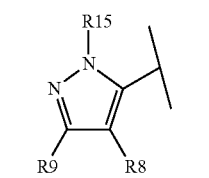 (aa)
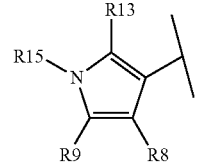 (ab)
-continued
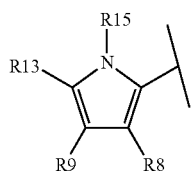 (ac)
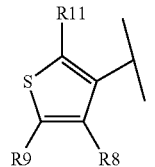 (ad)
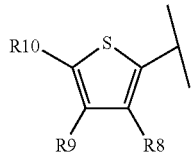 (ae)
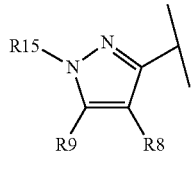 (af)
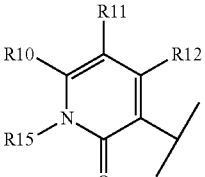 (ag)
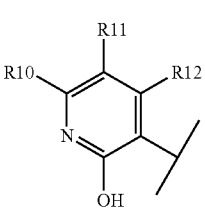 (ah)
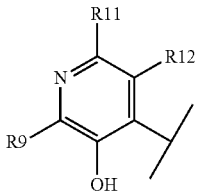 (ai)
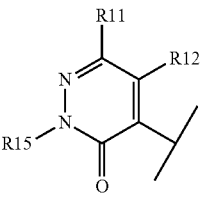 (aj)

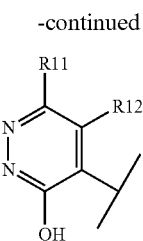

(ak)

in which R7, R8, R9, R10, R11, R12, R13, R14 and R15 have the meaning given hereinafter, R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents an R16 radical, a halogen, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16, R7a represents a hydrogen atom or an alkyl radical having from 1 to 5 carbon atoms, R8 represents a hydrogen atom, a halogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently chosen from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 or —CO$_2$R16 radical, or alternatively, when two of the R9, R10, R11 and R12 radicals are in the ortho position on an aromatic or heteroaromatic ring selected from the group consisting of the rings corresponding to formulae (p) to (z) and (aa) to (ak) above, then they can together form, with the bond which links them together, an aryl, heteroaryl, cycloalkyl or heterocycloalkyl ring, R13 and R14 are identical or different and are independently chosen from the group consisting of a hydrogen atom, a halogen atom, and an alkyl, —CF$_3$, —OCF$_3$, —OH, —SH, —CN, —SO$_2$R16, —SO$_2$NR16R17, —NHSO$_2$NR16R17, —NR16R17, —NR16CONR16R17, —NR16COR17, —NR16CO$_2$R17, —CONR16R17, —COR16 or —CO$_2$R16 radical, R15 represents a hydrogen atom or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X and X', which may be identical or different, represent an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

By way of example of compounds corresponding to general formula (I), mention may be made of the following compounds, without this list being limiting:

1/ 2-hydroxy-N,N-dimethyl-3-(2-{[(5-methylfuran-2-yl)-(tetrahydropyran-4-yl)methyl]amino}-3,4-dioxocyclobut-1-enylamino)benzamide 2/ 2-hydroxy-N,N-dimethyl-3-(2-{[(5-methylfuran-2-yl)-(tetrahydrothiopyran-4-yl)methyl]amino}-3,4-dioxocyclobut-1-enylamino)benzamide 3/ tert-butyl 4-[[2-(3-dimethylcarbamoyl-2-hydroxyphenylamino)-3,4-dioxocyclobut-1-enylamino]-(5-methylfuran-2-yl)methyl]piperidine-1-carboxylate 4/ benzyl 4-[[2-(3-dimethylcarbamoyl-2-hydroxyphenylamino)-3,4-dioxocyclobut-1-enylamino]-(5-methylfuran-2-yl)methyl]piperidine-1-carboxylate 5/ tert-butyl 3-[[2-(3-dimethylcarbamoyl-2-hydroxyphenylamino)-3,4-dioxocyclobut-1-enylamino]-(5-methylfuran-2-yl)methyl]piperidine-1-carboxylate 6/ 2-hydroxy-N,N-dimethyl-3-(2-{[(5-methylfuran-2-yl)-(4-methyltetrahydropyran-4-yl)methyl]amino}-3,4-dioxocyclobut-1-enylamino)benzamide.

In one preferred embodiment according to the invention, the compounds, and also the pharmaceutically acceptable salts, solvates or hydrates thereof, correspond to the above-mentioned general formula (I) in which:

R1 represents a hydrogen atom,

R2 represents a six-membered ring chosen from the structures (1), (5), (6) and (7) below:

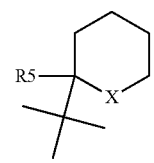

(1)

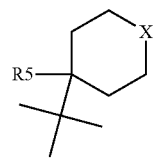

(5)

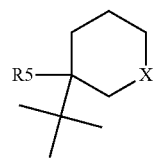

(6)

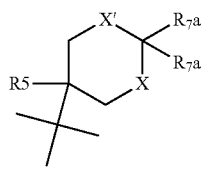

in which R5, X, X' and R7a have the meaning given hereinafter,

R3 represents an aromatic or heteroaromatic ring selected from the group consisting of the rings corresponding to formulae (a), (b) and (d) below:

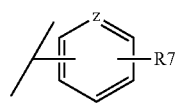

(a)

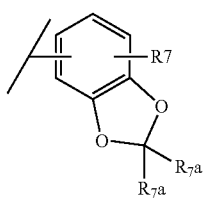

(b)

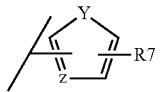

(d)

in which R7, R7a, Y and Z have the meaning given hereinafter, it being specified that the rings (a), (b) and (d) can optionally bear several R7 groups, which may be identical or different, the total number of such R7 groups being at most equal to the number of substitutable atoms of the ring;

R4 represents an aromatic or heteroaromatic ring selected from the group consisting of the rings corresponding to formulae (p), (q), (t), (z), (ad), (ag) and (ah) below:

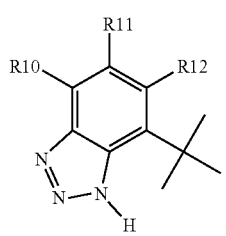

(p)

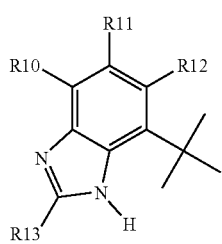

(q)

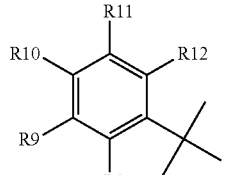

(t)

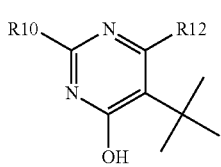

(z)

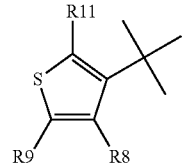

(ad)

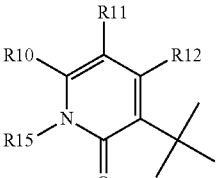

(ag)

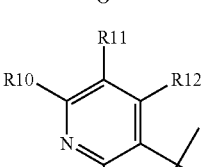

(ah)

in which R8, R9, R10, R11, R12, R13 and R15 have the meaning given hereinafter,

R5 represents a hydrogen atom, a fluorine atom, an alkyl radical comprising from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents an R16 radical, a halogen, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16, R7a represents a hydrogen atom or an alkyl radical containing from 1 to 5 carbon atoms, R8 represents a hydrogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently chosen from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 or —CO$_2$R16 radical, or alternatively, when two of the R9, R10, R11 and R12 radicals are in the ortho position on an aromatic or heteroaromatic ring selected from the group consisting of the rings corresponding to formulae (p), (q), (t), (z), (ad), (ag) and (ah) above, then they can together form, with the bond which links them together, an aryl, heteroaryl, cycloalkyl or heterocycloalkyl ring, R13 is chosen from the group consisting of a hydrogen atom, a halogen atom, and an alkyl, —CF₃, —OCF₃, —OH, —SH, —CN, —SO₂R16, —SO₂NR16R17, —NHSO₂NR16R17, —NR16R17, —NR16CONR16R17, —NR16COR17, —NR16CO₂R17, —CONR16R17, —COR16 or —CO₂R16 radical, R15 represents a hydrogen atom or an —OH, —SO₂R16, —COR16, —CO₂R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH₂COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X and X', which may be identical or different, represent an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

In one more particularly preferred embodiment according to the invention, the compounds, and also the pharmaceutically acceptable salts, solvates or hydrates thereof, correspond to the abovementioned formula (I), in which:

R1 represents a hydrogen atom,

R2 represents a six-membered ring chosen from the structures (5) and (6) below:

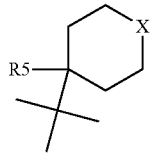

(5)

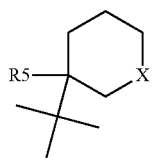

(6)

in which R5 and X have the meaning given hereinafter,

R3 represents a heteroaromatic ring corresponding to formula (d) below:

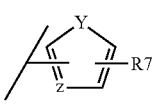

(d)

in which R7, Y and Z have the meaning given hereinafter, it being specified that the ring (d) can optionally bear several R7 groups, which may be identical or different, the total number of such R7 groups being at most equal to the number of substitutable atoms of the ring;

R4 represents an aromatic ring corresponding to formula (t) below:

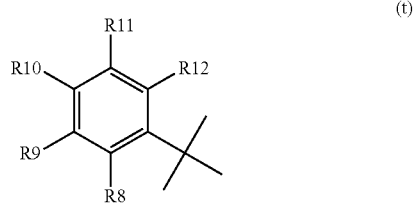

(t)

in which R8, R9, R10, R11 and R12 have the meaning given hereinafter,

R5 represents a hydrogen atom, a fluorine atom, an alkyl radical comprising from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a halogen atom, or an R16, —CF₃, —COR16, —OR16, —NR16R17, —NO₂, —CN, —SO₂R16, —SO₂NR16R17, —NR16COR17, —CONR16R17, —NR16CO₂R17 or —CO₂R16 radical, R8 represents a hydrogen atom, or an —OH, —SH, —CONHOR16, —CONR16OH, —NR16R17, —SO₃H, —OCOR16, —NHSO₂R16, —SO₂NR16R17, —NHCOR16, —CONR16R17, —NR16CO₂R17, —NHSO₂NR16R17, —CO₂R16, pyrrolyl, imidazolyl, triazolyl or tetrazolyl radical, R9, R10, R11 and R12 are identical or different and are independently chosen from the group consisting of a hydrogen atom, a halogen atom and an alkyl, alkoxy, —CF₃, —OCF₃, —OH, —NO₂, —CN, —SO₂R16, —SO₂NR16R17, —NR16COR17, —NR16CO₂R17, —CONR16R17, —COR16 or —CO₂R16 radical, or alternatively, when two of the R9, R10, R11 and R12 radicals are in the ortho position on an aromatic or heteroaromatic ring selected from the group consisting of the rings corresponding to formulae (p), (q), (t), (z), (ad), (ag) and (ah) above, they can together form, with the bond which links them together, an aryl, heteroaryl, cycloalkyl or heterocycloalkyl ring, R15 represents a hydrogen atom or an —OH, —SO₂R16, —COR16, —CO₂R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH₂COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

Among the compounds which are more particularly preferred, mention may be made, for example, of those chosen from the list comprising:

1/ 2-hydroxy-N,N-dimethyl-3-(2-{[(5-methylfuran-2-yl)-(tetrahydropyran-4-yl)methyl]amino}-3,4-dioxocyclobut-1-enylamino)benzamide 2/ 2-hydroxy-N,N-dimethyl-3-(2-{[(5-methylfuran-2-yl)-(tetrahydrothiopyran-4-yl)methyl]amino}-3,4-dioxocyclobut-1-enylamino)benzamide 6/ 2-hydroxy-N,N-dimethyl-3-(2-{[(5-methylfuran-2-yl)-(4-methyltetrahydropyran-4-yl)methyl]amino}-3,4-dioxocyclobut-1-enylamino)benzamide.

A second subject according to the invention relates to a pharmaceutical composition comprising an effective amount of a compound corresponding to general formula (I), or of a pharmaceutically acceptable salt of said compound as described above, in combination with a pharmaceutically acceptable solvent or support.

A third subject according to the invention relates to the compounds corresponding to general formula (I), and also the pharmaceutically acceptable salts, solvates or hydrates thereof, or else a pharmaceutical composition comprising an effective amount of a compound corresponding to general formula (I), or of one of the pharmaceutically acceptable salts thereof or one of the pharmaceutically acceptable solvates or hydrates thereof, for use as a medicament.

A fourth subject according to the invention relates to the compounds corresponding to general formula (I), and also the pharmaceutically acceptable salts, solvates or hydrates thereof, or else a pharmaceutical composition comprising an effective amount of a compound corresponding to general formula (I), or of one of the pharmaceutically acceptable salts thereof or one of the pharmaceutically acceptable solvates or hydrates thereof, for use in the treatment of α-chemokine-mediated diseases.

A fifth subject according to the invention relates to a method for treating α-chemokine-mediated diseases using a compound corresponding to general formula (I), and also the pharmaceutically acceptable salts, solvates or hydrates thereof, or else a pharmaceutical composition comprising an effective amount of a compound corresponding to general formula (I), or of one of the pharmaceutically acceptable salts thereof or one of the pharmaceutically acceptable solvates or hydrates thereof.

By way of examples of α-chemokine-mediated diseases, mention may be made of neutrophilic dermatosis, in particular psoriasis, atopic dermatitis, acne, rosacea, asthma, chronic obstructive pulmonary diseases, respiratory diseases in adults, arthritis, inflammatory bowel diseases, Crohn's disease, transplant rejection, cystic fibrosis and skin cancers.

The term "neutrophilic dermatosis" is intended to mean, in its broadest sense, Sweet's syndrome, "eccrine hydradenitis", SAPHO syndrome, Sneddon Wilkinson syndrome, pyoderma gangrenosum, erythema elevatum duitinum, psoriasis, common psoriasis, pustular psoriasis, palmoplantar pustulosis, exanthematous pustulosis (AGEP), pustulosis with vasculitis, acropustulosis of infancy, Behcet's disease, and also certain bullous diseases such as herpes derived in the form of dermatitis, neutophilic IgA dermatosis, intraepidermal IgA pustulosis, bullous pemphigoid, IgA pemphigus, vasculitis, Leroy Reiter Fiellinger syndrome, pustulosis of the scalp, acrodermatitis continua of Hallopeau and dermatosis related to angioimmunoblastic lymphadenopathy, with cyclophosphamid-induced dysmyelopoiesis, with p-ANCA antibodies.

In one preferred embodiment according to the invention, the compound or the pharmaceutical composition mentioned above is used in the treatment of skin diseases such as neutrophilic dermatosis, in particular psoriasis, atopic dermatitis, acne and rosacea.

Another aspect of the invention relates to the use of a compound corresponding to general formula (I), and also the pharmaceutically acceptable salts, solvates or hydrates thereof, or else the use of a pharmaceutical composition comprising an effective amount of a compound corresponding to general formula (I), or of one of the pharmaceutically acceptable salts thereof or one of the pharmaceutically acceptable solvates or hydrates thereof, for preparing a medicament for the treatment of diseases of the group comprising neutrophilic dermatosis, in particular psoriasis, atopic dermatitis, acne, rosacea, asthma, chronic obstructive pulmonary diseases, respiratory diseases in adults, arthritis, inflammatory bowel diseases, Crohn's disease, transplant rejection, cystic fibrosis and skin cancers.

The compounds of general formula (I) of the present invention are prepared according to one or more of the synthesis routes as described below or as emerge from the various preparation examples given hereinafter in a nonlimiting manner.

The general synthesis route for preparing the compounds of formula (III) is illustrated in scheme 1. Sequential treatment of the alkyl squarates intermediates (A) with the amines R'2-$NH_2$ and R'3-$NH_2$ gives the compounds of formula (III). In formula (A), R'1 is a $C_1$-$C_6$ alkyl, preferably methyl or ethyl. The reaction is carried out in an inert and polar solvent (or in a mixture of solvents), such as ethanol, methanol, dimethyl sulfoxide, dimethylformamide or acetonitrile. The amines R'2-$NH_2$ and R'3-$NH_2$ can be used as free bases or in salt form. The reactions can be carried out in the presence of a suitable base, such as triethylamine, diisopropylethylamine, sodium carbonate or potassium carbonate and at 25° C. or preferably at high temperatures of 50-80° C. The reaction time is generally between 1 hour and 72 hours so as to have complete conversion.

The amines R'3-$NH_2$ of formula (IX) are prepared according to scheme 2 from commercial reagents using methods well known to those skilled in the art, described in the organic synthesis manuals, for instance "Comprehensive Organic Functional Group Transformation" Vol. 1-7 A. R. Katritzky, O. Meth-Cohn, C. W. Rees, Pergamon Press, 1998.

The primary alcohols (IV) [in which X and R have the same meaning as X and R5 respectively defined above for the compounds of general formula (I)] are oxidized to aldehydes of formula (V) under the conditions of Swern (Mancuso, A. J.; Huang, S.-L.; Swern, D. (1978). "Oxidation of long-chain and related alcohols to carbonyls by dimethyl sulfoxide "activated" by oxalyl chloride" *J. Org. Chem.* 43 (12), 2480-2482) or with pyridinium chlorochromate.

The aldehyde of formula (V) is successively treated with an aryl or heteroaryl Grignard reagent or with a lithiated derivative to give a secondary alcohol of formula (VI). The corresponding azides (VII) are prepared from the alcohols (VI) either by converting them into mesylates (VIII) which are subsequently treated with metal azides (for example sodium azide), or by converting them directly into an azide after treatment with diphenylphosphoryl azide (DPPA). The azide (VII) is finally reduced to the corresponding amine (IX) with hydrogen in the presence of various catalysts (for example, palladium on activated carbon) or by treatment with triphenylphosphine followed by hydrolysis of the imidophosphorane intermediates (Gololobov, Y. G. (1981), "Sixty years of staudinger reaction", *Tetrahedron* 37 (3), 437).

Alternatively, the primary amines R'3-NH$_2$ of formula (IX) can be prepared according to scheme 3 from commercial acids (X) [in which X and R have the same meaning as X and R5 respectively defined above for the compounds of general formula (I)], by converting them to Weinreb amides (XI) (Nahm, S.; Weinreb, S. M. (1981), "N-methoxy-n-methylamides as effective acylating agents", *Tetrahedron Letters* 22, 3815), which, after reaction with aryl or heteroaryl Grignard reagents or with lithiated aryl or heteroaryl derivatives give the ketones (XII) which can be reduced to secondary alcohols (VI).

By following the steps described in scheme 2, the alcohol (VI) is optionally converted to the amine R'3-NH$_2$ of formula (IX).

The chiral primary amine R'3-NH$_2$ having the structure (XV) can also be prepared according to scheme 4 by condensation of enantiomerically pure 2-methyl-2-propanesulfinamide (tert-butanesulfinamide, Elman's sulfinamide: Liu, G. et al. *J. Am. Soc. Chem.* 1997, 119, 9913) with the aldehyde (IV) under mild conditions. This reaction gives the tert-butanesulfinylimines (XIII). The tert-butanesulfinyl group activates the imines for the addition of the Grignard reagents and serves as an important chiral directing group for giving the products (XIV) with high diastereoselectivity. Deprotection of the tert-butanesulfinyl group under mild acidic conditions gives the chiral amine (XV).

The amide derivatives of 3-aminosalicylic acid of formula (XVIII) are prepared according to scheme 5a/ from 3-nitrosalicylic acid (XVI) using standard peptide coupling conditions, followed by reduction of the nitro group to an amino group with hydrogen in the presence of an appropriate catalyst (for example, palladium on activated carbon). The derivative (XVIII) then reacts with commercial dimethoxysquarate or diethoxysquarate to give the intermediate (XIX), which is converted to compound (XX) after reaction with the primary amine R'3-NH$_2$. Alternatively, the coupling of the 3-aminosalicylic acid (XXI) with commercial dimethyl or diethyl squarate gives, according to scheme 5b/, the intermediate acid derivative (XXII) which, after reaction with the primary amine R'3-NH$_2$, can give the compound (XXIII). The latter can, finally, be used in a peptide coupling reaction with an amine of formula RaRbNH to give the compound of formula (XX).

By way of illustration, the following compounds corresponding to general formula (I) of the present invention were prepared according to one of the schemes presented above.

Example 1

Preparation of 2-hydroxy-N,N-dimethyl-3-(2-{[(5-methylfuran-2-yl)-(tetrahydropyran-4-yl)methyl]amino}-3,4-dioxocyclobut-1-enylamino)benzamide

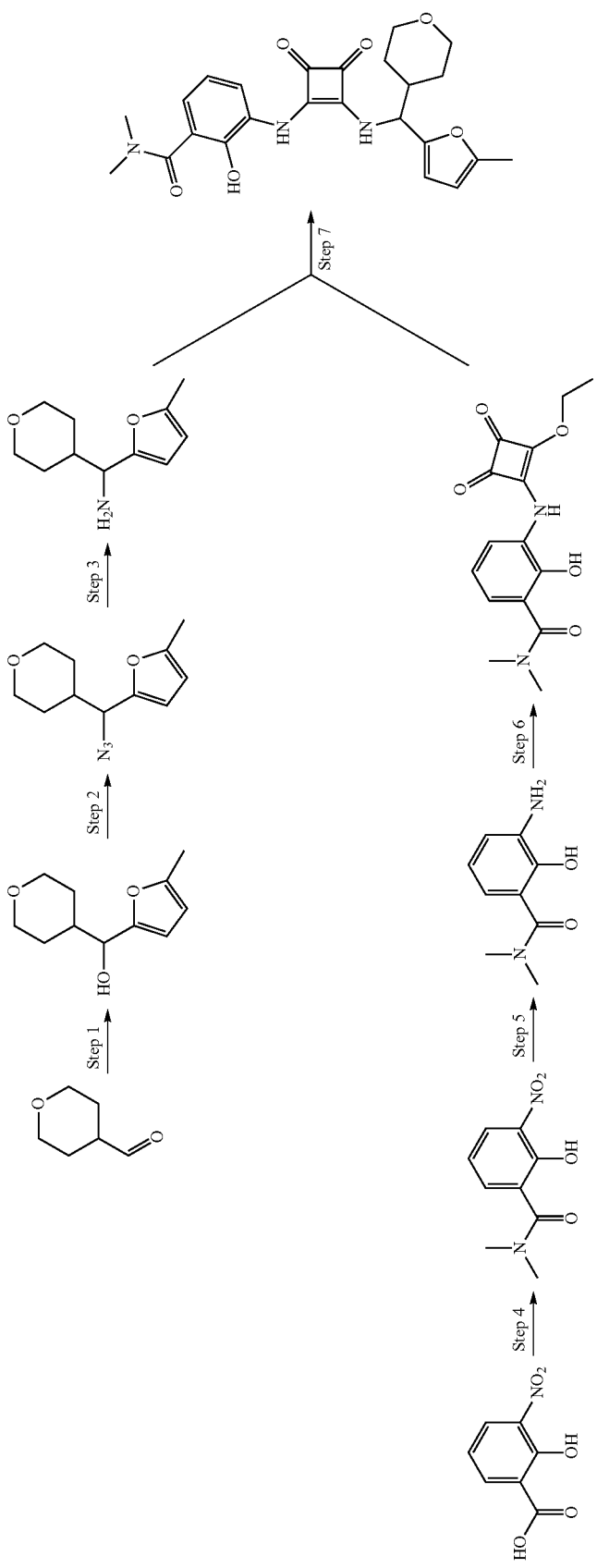

Step 1

(5-Methylfuran-2-yl)-(tetrahydropyran-4-yl)methanol 12.0 ml (30 mmol, 1.5 eq) of a 2.5 M solution of n-butyllithium in hexane were added dropwise to a solution of 2.46 g (30 mmol, 1.5 eq) of 2-methylfuran in 50 ml of tetrahydrofuran cooled to −70° C. The reaction medium was stirred and allowed to return to ambient temperature for 2 hours. The reaction medium was cooled to −70° C. and then 2.28 g (20 mmol, 1 eq) of tetrahydro-2H-pyran-4-carbaldehyde were added. The reaction medium was stirred at ambient temperature for 2 hours. The reaction medium was treated with a saturated ammonium chloride solution and extracted with ethyl acetate. The organic phases were combined, washed with a saturated sodium chloride solution and evaporated. 4.43 g of (5-methylfuran-2-yl)-(tetrahydropyran-4-yl)methanol were obtained. Yield=100%.

Step 2

4-[Azido-(5-methylfuran-2-yl)methyl]tetrahydropyran 6.08 g (22 mmol, 1.1 eq) of diphenylphosphoryl azide were added dropwise to a solution of 4.43 g (20 mmol, 1 eq) of (5-methylfuran-2-yl)-(tetrahydropyran-4-yl)methanol at 89% in 60 ml of toluene. The reaction medium was cooled to 0° C. and then 3.3 ml (22 mmol, 1.1 eq) of 1,8-diazabicyclo[5.4.0]undec-7-ene were added dropwise. The reaction medium was stirred at ambient temperature for 22 hours. The reaction medium was separated by settling out and the organic phase was washed with water and then with 1 N hydrochloric acid, dried over magnesium sulfate, filtered and evaporated. The residue was chromatographed on silica gel (column Analogix SF40-240 g, Spot II) eluted with heptane/ethyl acetate (95/5). 3.09 g of 4-[azido-(5-methylfuran-2-yl)methyl]tetrahydropyran were obtained. Yield=70%.

Step 3

C-(5-Methylfuran-2-yl)-C-(tetrahydropyran-4-yl)methylamine

A solution of 3.09 g (14 mmol, 1 eq) of 4-[azido-(5-methylfuran-2-yl)methyl]tetrahydropyran in 60 ml of ethanol in the presence of 470 mg (15% by weight) of palladium on carbon at 10% was stirred at hydrogen atmospheric pressure for 17 hours. The reaction medium was filtered and the filtrate was evaporated. 2.715 g of C-(5-methylfuran-2-yl)-C-(tetrahydropyran-4-yl)methylamine were obtained. Yield=99%.

Step 4

2-Hydroxy-N,N-dimethyl-3-nitrobenzamide 42.9 ml (0.50 mol, 3 eq) of oxalyl chloride were added dropwise to a suspension of 30 g (0.16 mol, 1 eq) of 3-nitrosalicylic acid in 1200 ml of dichloromethane. 30 drops of N,N-dimethylformamide were added (large amount of gas given off, adaptation of a system for trapping toxic carbon monoxide vapors). The reaction medium was stirred at ambient temperature for 24 hours. The reaction medium was cooled to 0-5° C. and then 246 ml (0.49 mol, 3 eq) of a 2 N solution of dimethylamine in tetrahydrofuran were added. The reaction medium was stirred at ambient temperature for 2 days. The reaction medium was concentrated to dryness and the residue was dissolved in 300 ml 1 N sodium hydroxide. The aqueous solution (red) was extracted 3 times with 300 ml of dichloromethane. The aqueous phase was cooled in a water-ice bath, and the pH was adjusted to 2 with approximately 50 ml of 6 N hydrochloric acid. The mixture (which had become yellow) was extracted 3 times with 300 ml of dichloromethane. The organic phases were combined, washed twice with 250 ml of water and then once with 250 ml of a saturated sodium chloride solution, dried over anhydrous magnesium sulfate and evaporated. 33.5 g of 2-hydroxy-N,N-dimethyl-3-nitrobenzamide were obtained in the form of a yellow cotton solid. Yield=97%.

Step 5

3-Amino-2-hydroxy-N,N-dimethylbenzamide

A solution of 33.5 g of 2-hydroxy-N,N-dimethyl-3-nitrobenzamide in 600 ml of ethanol were added to a suspension of 3.35 g of Pd/C 10% in 70 ml of ethanol. The reaction medium was stirred under 2 bar of hydrogen overnight. TLC and HPLC control (t=0.66 M+181). The reaction medium was filtered through celite and the filtrate was evaporated. 29 g of 3-amino-2-hydroxy-N,N-dimethylbenzamide were obtained in the form of an oily brown solid. Yield=100%.

Step 6

3-(2-Ethoxy-3,4-dioxocyclobut-1-enylamino)-2-hydroxy-N,N-dimethylbenzamide

Under nitrogen and at ambient temperature, 39.7 g of diethoxysquarate were added (over the course of 15 minutes) to a solution of 28 g of 3-amino-2-hydroxy-N,N-dimethylbenzamide in 840 ml of ethanol cooled to 0° C. The reaction medium was stirred for 2 hours at 0° C. and 48 hours at ambient temperature. 700 ml of ethanol were added (which increases the precipitation of the expected product). The solid was filtered off, washed with ambient ethanol and dried. 36.9 g of (2-ethoxy-3,4-dioxocyclobut-1-enylamino)-2-hydroxy-N,N-dimethylbenzamide were obtained in the form of a light khaki green solid. Yield=78%.

Step 7

2-Hydroxy-N,N-dimethyl-3-(2-{[(5-methylfuran-2-yl)-(tetrahydropyran-4-yl)methyl]amino}-3,4-dioxocyclobut-1-enylamino)benzamide 644 mg (3.3 mmol, 2 eq) of C-(5-methylfuran-2-yl)-C-(tetrahydropyran-4-yl)methylamine were added to 500 mg (1.64 mmol, 1 eq) of 3-(2-ethoxy-3,4-dioxocyclobut-1-enylamino)-2-hydroxy-N,N-dimethylbenzamide dissolved under hot conditions in 50 ml of methanol. The reaction medium was stirred at ambient temperature for 21 hours. The methanol was evaporated off and the residue (green oil) was chromatographed on silica gel (column Analogix SF15-40 g, Spot II) eluted with dichloromethane/methanol (gradient). 700 mg of 2-hydroxy-N,N-dimethyl-3-(2-{[(5-methylfuran-2-yl)-(tetrahydropyran-4-yl)methyl]amino}-3,4-dioxocyclobut-1-enylamino)benzamide were obtained. (M.p.=137-140° C.). Yield=94%. LC/MS: 97.1% [453]

$^1$H NMR (DMSO-d6, 400 MHz): 1.22-1.38 (m, 3H); 1.63 (d, J=0.12, 1H); 2.09 (m, 1H); 2.28 (s, 3H); 2.94 (s, 6H); 3.28 (dd, J=11.6, 2H); 3.8-3.9 (2dd, J=11.28 Hz, 2H); 5.08 (t, 1H);

6.06 (d, J=3.0 Hz, 1H), 6.27 (d, J=3.1 Hz, 1H); 6.85-6.90 (m, 2H); 7.78 (dd, J=7.0 Hz, 1H); 8.7 (d, J=9.5 Hz, 1H); 9.37 (s, 1H); 9.9 (s, 1H).

Example 2

Preparation of 2-hydroxy-N,N-dimethyl-3-(2-{[(5-methylfuran-2-yl)-(tetrahydrothiopyran-4-yl)methyl]amino}-3,4-dioxocyclobut-1-enylamino)benzamide

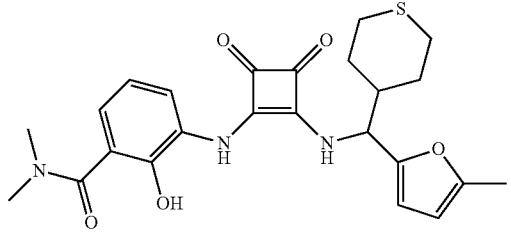

Step 1

In a manner analogous to EXAMPLE 1 (Method A, step 1), (5-methylfuran-2-yl)-(tetrahydrothiopyran-4-yl)methanol was prepared. Yield=86%.

Step 2

In a manner analogous to EXAMPLE 1 (Method A, step 2), 2-[azido(tetrahydrothiopyran-4-yl)methyl]-5-methylfuran was prepared. Yield=40%.

Step 3

C-(5-Methylfuran-2-yl)-C-(tetrahydrothiopyran-4-yl)methylamine 304 mg (8 mmol, 2 eq) of lithium aluminum hydride were added to a solution of 968 mg (4 mmol, 1 eq) of 2-[azido(tetrahydrothiopyran-4-yl)methyl]-5-methylfuran in 10 ml of tetrahydrofuran cooled to −10° C. The reaction medium was stirred at ambient temperature for 2 hours. The reaction medium was cooled to 0° C. and water with a solution of sodium hydroxide at 2 N and diethyl ether were added (precipitation of the aluminum and lithium salts). The reaction medium was filtered through celite and then the filtrate was treated with a 3 N hydrochloric acid solution. The aqueous phase was recovered and basified with a 15 N sodium hydroxide solution and then extracted with diethyl ether. The organic phases were combined, dried over magnesium sulfate, filtered and evaporated. 728 mg of C-(5-methylfuran-2-yl)-C-(tetrahydrothiopyran-4-yl)methylamine were obtained. Yield=86%.

Steps 4 to 7

In a manner analogous to EXAMPLE 1 (Method A, steps 3 to 7), 2-hydroxy-N,N-dimethyl-3-(2-{[(5-methylfuran-2-yl)-(tetrahydrothiopyran-4-yl)methyl]amino}-3,4-dioxocyclobut-1-enylamino)benzamide was prepared. (M.p.=173-175° C.). LC/MS: 98.81% [469]

$^1$H NMR (DMSO-d6, 400 MHz): 1.30-1.40 (m, 2H); 1.84-1.93 (m, 2H); 2.02 (d, J=11.1, 1H); 2.28 (s, 3H); 2.56-2.68 (m, 4H); 2.94 (s, 6H); 3.37 (m, 1H); 5.12 (t, 1H); 6.06 (d, J=2.0 Hz, 1H), 6.25 (d, J=3.0 Hz, 1H); 6.85-6.90 (m, 2H); 7.78 (dd, J=7.0 Hz, 1H); 8.7 (d, J=9.6 Hz, 1H); 9.4 (s, 1H).

Example 3

Preparation of tert-butyl 4-[[2-(3-dimethylcarbamoyl-2-hydroxyphenylamino)-3,4-dioxocyclobut-1-enylamino]-(5-methylfuran-2-yl)methyl]piperidine-1-carboxylate

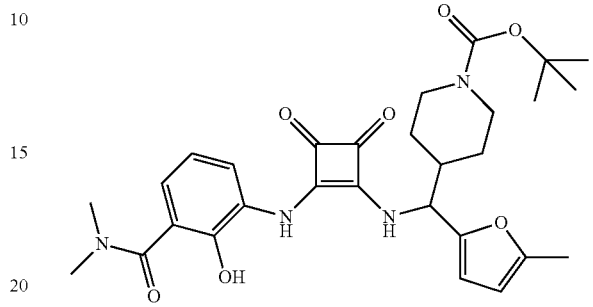

Steps 1 to 7

In a manner analogous to EXAMPLE 1 (Method A, steps 1 to 7), and using tert-butyl 4-formylpiperidene-1-carboxylate, tert-butyl 4-[[2-(3-dimethylcarbamoyl-2-hydroxyphenylamino)-3,4-dioxocyclobutenylamino]-(5-methylfuran-2-yl)methyl]piperidine-1-carboxylate was prepared. HPLC 99.42%, ES+ [553].

$^1$H NMR (DMSO-d6, 400 MHz): 1.00-1.25 (m, 2H); 1.38 (s, 9H); 1.45-1.50 (m, 1H); 1.65-1.75 (m, 1H); 1.90-2.10 (m, 1H); 2.28 (s, 3H); 2.60-2.85 (bs, 2H); 2.94 (s, 6H); 3.90-4.10 (m, 2H); 5.10 (t, 1H); 6.06 (s, 1H); 6.27 (s, 1H); 6.87-6.89 (m, 2H); 7.80 (d, 1H); 8.70 (d, 1H); 9.37 (s, 1H); 10.00 (s, 1H).

Example 4

Preparation of benzyl 4-[[2-(3-dimethylcarbamoyl-2-hydroxyphenylamino)-3,4-dioxocyclobut-1-enylamino]-(5-methylfuran-2-yl)methyl]piperidine-1-carboxylate

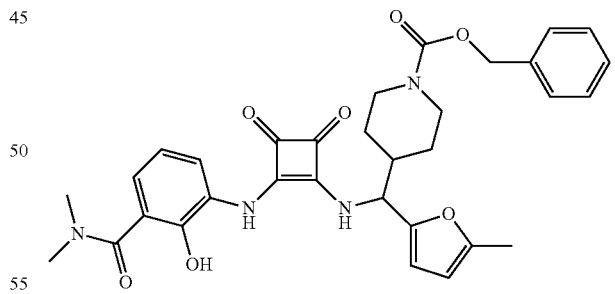

Steps 1 to 7

In a manner analogous to EXAMPLE 1 (Method A, steps 1 to 7), and using benzyl 4-formylpiperidene-1-carboxylate, benzyl 4-[[2-(dimethylcarbamoyl-2-hydroxyphenylamino)-3,4-dioxocyclobut-1-enylamino]-(5-methylfuran-2-yl)methyl]piperidine-1-carboxylate was prepared. HPLC 99.11%, ES+ [586].

$^1$H NMR (DMSO-d6, 400 MHz): 1.07-1.20 (m, 2H); 1.45-1.55 (m, 1H); 1.70-1.80 (m, 1H); 2.00-2.10 (m, 1H); 2.28 (s, 3H); 2.70-2.90 (s, 2H); 2.94 (s, 6H); 4.0-4.10 (m, 2H); 5.06 (s,

2H); 5.08-5.13 (m, 1H); 6.07 (s, 1H); 6.27 (s, 1H); 6.85-6.91 (m, 2H); 7.28-7.38 (m, 5H); 7.78 (d, 1H); 8.72 (d, 1H); 9.39 (s, 1H); 10.00 (s, 1H).

Example 5

Preparation of tert-butyl 3-[[2-(3-dimethylcarbamoyl-2-hydroxyphenylamino)-3,4-dioxocyclobut-1-enylamino]-(5-methylfuran-2-yl)methyl]piperidine-1-carboxylate

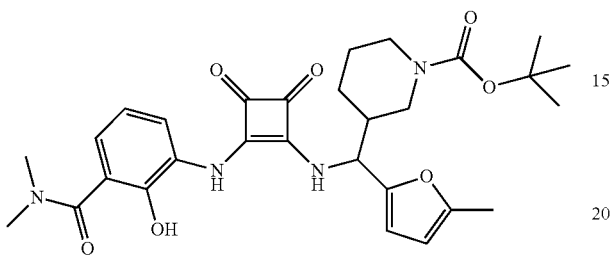

Steps 1 to 7

In a manner analogous to EXAMPLE 1 (Method A, steps 1 to 7), and using tert-butyl 3-formylpiperidene-1-carboxylate, tert-butyl 3-[[2-(3-dimethylcarbamoyl-2-hydroxyphenylamino)-3,4-dioxocyclobutenylamino]-(5-methylfuran-2-yl)methyl]piperidine-1-carboxylate was prepared. The two diastereoisomers were separated by chromatography on silica gel, eluted with dichloromethane/methanol (95/5).

Diastereoisomer 1: Column Kinetex 150×3 mm, 2.6 mic, reverse phase, retention time 14.09 min. HPLC 99.8%, ES+ [552+Na]

$^1$H NMR (DMSO-d6, 400 MHz): 1.36 (bs, 10H); 1.67 (bs, 2H); 1.90-1.96 (m, 1H); 2.29 (s, 3H); 2.94 (s, 6H); 3.40-3.90 (m, 3H); 5.08 (bs, 1H); 6.08 (s, 1H); 6.28 (s, 1H); 6.85-6.91 (m, 2H); 7.78-7.80 (m, 1H); 7.75 (d, 1H); 9.33 (s, 1H); 9.95 (s, 1H).

Diastereoisomer 2: Column Kinetex 150×3 mm, 2.6 mic, reverse phase, retention time 13.9 min. HPLC 99.3%, ES+ [552+Na]

$^1$H NMR (DMSO-d6, 400 MHz): 1.15-1.45 (m, 12H); 1.57 (bs, 2H); 1.95-1.99 (m, 1H); 2.28 (s, 3H); 2.94 (s, 6H); 3.40-4.10 (m, 3H); 5.15 (bs, 1H); 6.06 (s, 1H); 6.27 (s, 1H); 6.85-6.90 (m, 2H); 7.78-7.81 (m, 1H); 7.81 (d, 1H); 9.35 (s, 1H); 10.00 (s, 1H).

Example 6

Preparation of 2-hydroxy-N,N-dimethyl-3-(2-{[(5-methylfuran-2-yl)-(4-methyltetrahydropyran-4-yl)methyl]amino}-3,4-dioxocyclobut-1-enylamino) benzamide

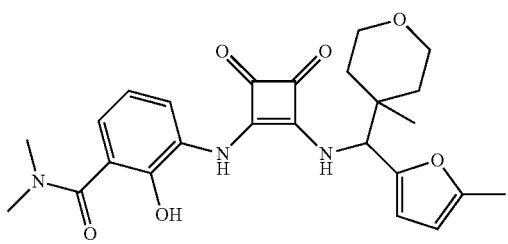

Steps 1 to 7

In a manner analogous to EXAMPLE 1 (Method A, steps 1 to 7), and using 4-methyltetrahydropyran-4-carbaldehyde, 2-hydroxy-N,N-dimethyl-3-(2-{[(5-methylfuran-2-yl)-(4-methyltetrahydropyran-4-yl)methyl]amino}-3,4-dioxocyclobutenylamino)benzamide was prepared. HPLC 99.42%, ES+ [553]

$^1$H NMR (DMSO-d6, 400 MHz): 1.00-1.25 (m, 2H); 1.38 (s, 9H); 1.45-1.50 (m, 1H); 1.65-1.75 (m, 1H); 1.90-2.10 (m, 1H); 2.28 (s, 3H); 2.60-2.85 (s, 2H); 2.94 (s, 6H); 3.90-4.10 (m, 2H); 5.10 (t, 1H); 6.06 (s, 1H); 6.27 (s, 1H); 6.87-6.89 (m, 2H); 7.80 (d, 1H); 8.70 (d, 1H); 9.37 (s, 1H); 10.00 (s, 1H).

Biological Tests

Example 7

In Vitro Affinity

The in vitro affinity of the compounds of the present invention for the CXCR1 and CXCR2 receptors was determined on a functional test of the β-arrestin recruitment after receptor activation type.

It was demonstrated that the activation by CXCL8 of the CXCR2 receptor in cells of the PathHunter HEK293-CXCR2 line or of the CXCR1 receptor in cells of the U2OS h CXCR1 β-arrestin line results in the recruitment of β-arrestin (Richardson et al. 2003 Role of the cytoplasmic tails of CXCR1 and CXCR2 in mediating leukocyte migration, activation, and regulation.>>J. Immunol. 170: 2904-2911).

In order to evaluate the direct interaction of the CXCR2 or CXCR1 receptor with β-arrestin 2, a β-arrestin 2 recruitment test for CXCR2 or CXCR1 based on β-galactosidase enzyme complementation (Olson K R, Eglen R M. Beta galactosidase complementation: a cell-based luminescent assay platform for drug discovery. Assay Drug Dev Technol. 2007 February; 5(1); 137-44), as established by DiscoveRx Corporation was used. The stimulation of these two cell lines with CXCL8 (10 nM) induces β-arrestin 2 recruitment, as indicated by a significant increase in the induction factor. All the CXCR2 antagonists were tested in a dose-dependent manner and the concentration corresponding to 50% inhibition of the response was determined ($IC_{50}$=half inhibition concentration).

β-Arrestin Recruitment Assay:

"PathHunter HEK293-CXCR2" or "U2OS hCXCR1 β-arrestin" cells (DiscoveRx Corporation) were seeded overnight at 10 000 cells/well (384-well format) in 20 μl of Opti MEM I medium. A preincubation with the antagonist or the vehicle for 30 min at 37° C. and 5% $CO_2$ was followed by 60 minutes of stimulation with CXCL8 at 37° C. and 5% $CO_2$. The cells were then placed at ambient temperature for 30 minutes. The PathHunter detection reagent (DiscoveRx Corporation) was added. After incubation for 60 min at ambient temperature, the β-galactosidase induced by the luminescence during the β-arrestin-CXCR2 interaction was measured for 0.3 s in an Envision 2102 Multilabel Reader (PerkinElmer Life and Analytical Sciences). The data were analyzed by means of a non-linear curve procedure using the XLFit4 exploitation software (IDBS) and the IC50 values were determined.

| Compound (Example No.) | CXCR1 (nM) | CXCR2 (nM) |
|---|---|---|
| 1 | 5440 | 212 |
| 2 | 3391 | 111 |
| 6 | 3350 | 157 |

Example 8

Polypharmacology: "Receptor Profiling"

Measurement of Calcium Flux on Cells:

The experiments were carried out on the FLIPR TETRA® platform from Molecular Devices. After the basal level had been read, the compounds were added to the cells expressing the chemokine receptor of interest and the agonist activity was read at 10 seconds. After a further incubation for 10 minutes, the cells were activated, with a concentration equivalent to the AC80, using a reference agonist in order to detect whether this compound exhibits antagonist activity.

Each cell line expressing a chemokine receptor was established on the basis of the Chem-1 cell stably expressing the recombinant form of the chemokine receptor and also an associated G protein, with the aim of coupling the receptor to the calcium signaling pathway.

21 receptors belonging to the chemokine receptor family (CCRs and CXCRs) were analyzed. All the CXCR2 antagonists were tested in a dose-dependent manner and the concentration corresponding to 50% inhibition of the response was determined ($IC_{50}$).

Example 9

Dissociation Constant

The determination of the half-dissociation constants of the CXCR2 antagonists was based on the in vitro β-arrestin recruitment model previously described: "PathHunter HEK293-CXCR2" cells (DiscoveRx Corporation) were seeded overnight at 20 000 cells/well (in a 96-well format) in 100 µl/well of OptiMEM culture medium-1% FCS. A preincubation with the antagonist or the vehicle was carried out for 1 hour at 37° C.-5% $CO_2$. The cells were then washed 3 times with 100 µl/well of OptiMEM medium-1% FCS and then a variable incubation (0 h-0.5 h-6 h-12 h-24 h) of the cells at 37° C.-5% $CO_2$ was carried out. The cells were then stimulated with 4 nM of CXCL8 at 37° C.-5% $CO_2$ for 1 h 30 min. The PathHunter detection reagent (DiscoveRx Corporation) was added in a proportion of 50 µl/well. After incubation for 60 minutes at ambient temperature, the luminescence emitted, via the hydrolysis of the substrate by the β-galactosidase complemented during the β-arrestin-CXCR2 interaction, was measured for 0.3 seconds/well with an Envision Multilabel Reader (PerkinElmer Life and Analytical Sciences). The data were analyzed by means of a non-linear curve procedure using the XLFit4 exploitation software (IDBS) and the IC50 values were determined. The half-dissociation time was determined on a regression of type $y=(A*(1-\exp(((-1)*B)*x)))$ (where x=time and y=standardized luminescence) at saturating concentration of antagonist.

Results: The molecules described in the present invention were compared to the SCH5217123 molecule (described as having a pseudo-irreversible dissociation) (Pharmacological Characterization of Sch527123, a Potent Allosteric CXCR1/CXCR2 Antagonist. JPET 322:477-485, 2007).

Example 10

A/ Metabolic Stabilities in Hepatic Microsomes

Hepatic microsomes (Becton Dickinson) were incubated at a protein concentration of 0.5 mg/ml in the reaction medium.

The reaction medium of the microsomes was composed of phosphate buffer, pH: 7.4 at 100 mM, of $MgCl_2$ at 100 mM (50/50), of an ATP-generating system composed of a mixture of nicotinamide adenine diphosphate (NADP) and of glucose-6-phosphate (G6P) at 1 mg/ml and of glucose-6-phosphate dehydrogenase (G6PDH) at 4 U/ml. The compounds were tested at 1 µM (0.1% DMSO).

The samples of incubation medium after addition of the microsomes were taken at times 5, 10, 15, 30 and 60 minutes. At each time, the metabolic reaction was stopped by adding methanol (1 volume incubation medium/3 volumes of methanol). The disappearance of the parent product was measured by LC/MS/MS analysis. The time for which 50% of parent product disappeared (T½) was calculated from the kinetics of disappearance of the parent product as a function of time.

B/ Metabolic Stabilities in Hepatocytes

The human hepatocytes were supplied by Biopredic in 24-well plates. After 48 h of adaptation in culture, the hepatocytes were placed in a treatment medium containing 0.1% bovine serum albumin, and the compounds were tested at 1 µM (0.1% DMSO).

The samples of incubation medium after addition of the test compound were taken at times t=0, 1, 2, 4, 6 and 24 hours.

At each time, the metabolic reaction was stopped by adding methanol (1 volume incubation medium/3 volumes of methanol). The disappearance of the parent product was measured by LC/MS/MS analysis. The time for which 50% (T½) of parent product disappeared was calculated from the kinetics of disappearance of the parent product as a function of time.

The invention claimed is:

1. A disubstituted 3,4-diamino-3-cyclobutene-1,2-dione compound corresponding to general formula (I) below, or one of the pharmaceutically acceptable salts or solvates thereof:

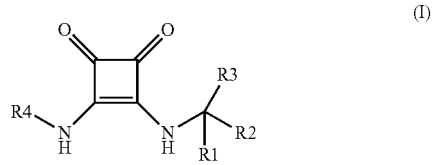

(I)

in which,

R1 represents a hydrogen atom or a methyl,

R2 represents a six-membered ring chosen from the structures (1) to (7) below:

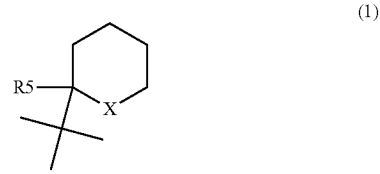

(1)

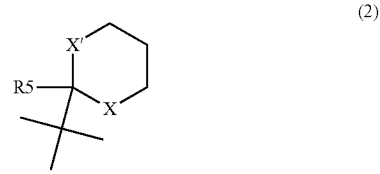

(2)

-continued (3)
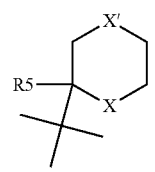

(4)
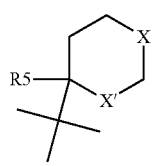

(5)
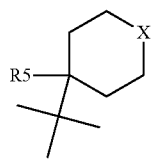

(6)
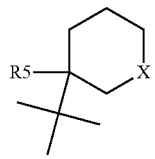

(7)
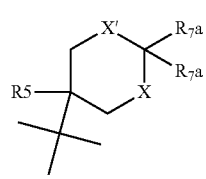

in which R5, X, X' and R7a have the meaning given hereinafter,

R3 represents an aromatic or heteroaromatic ring selected from the group consisting of the rings corresponding to formulae (a) to (o) below:

(a)
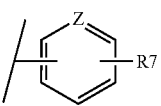

(b)
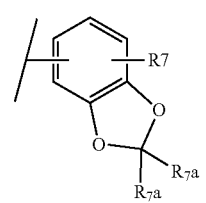

(c)
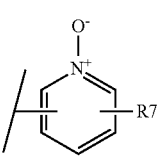

-continued (d)
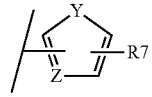

(e)
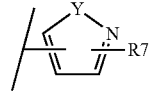

(f)
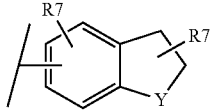

(g)
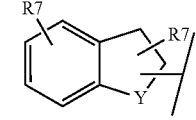

(h)
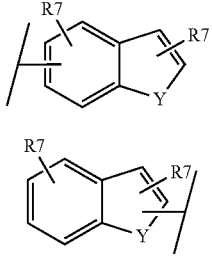

(i)

(j)
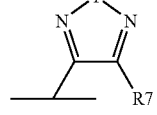

(k)
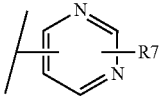

(l)

(m)

(n)
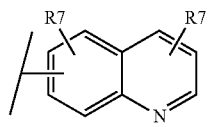

(o)

in which R7, R7a, Y and Z have the meaning given hereinafter, it being specified that the rings (a) to (o) can optionally bear several R7 groups, which may be identical or different, the total number of such R7 groups being at most equal to the number of substitutable atoms of the ring;
R4 represents an aromatic or heteroaromatic ring selected from the group consisting of the rings corresponding to formulae (p) to (z) and (aa) to (ak) below:
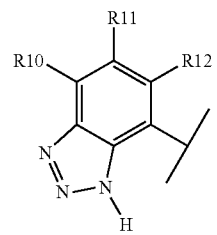 (p)
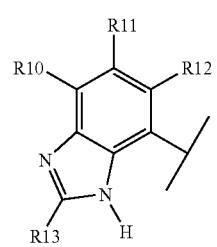 (q)
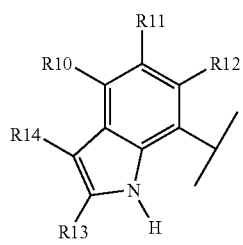 (r)
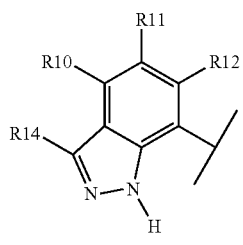 (s)
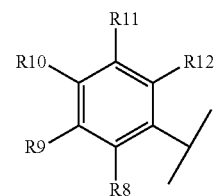 (t)
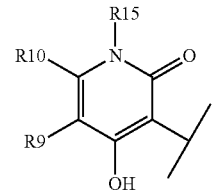 (u)
-continued
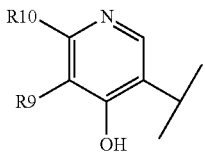 (v)
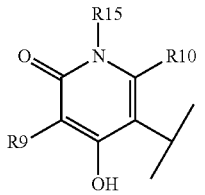 (w)
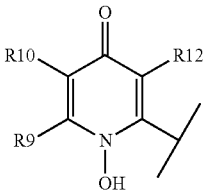 (x)
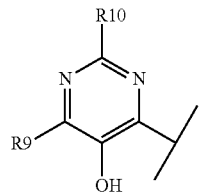 (y)
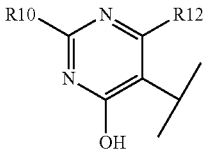 (z)
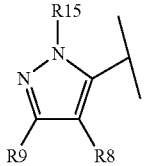 (aa)
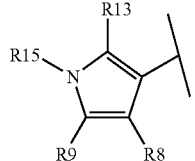 (ab)
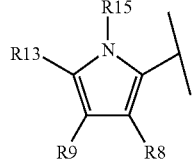 (ac)

-continued (ad) 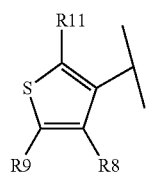

(ae) 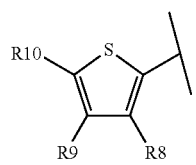

(af) 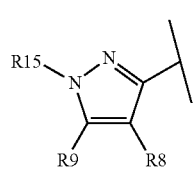

(ag) 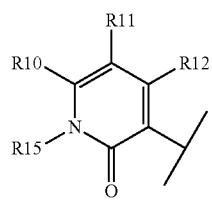

(ah) 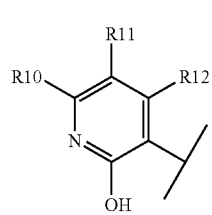

(ai) 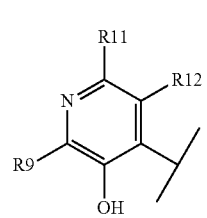

(aj) 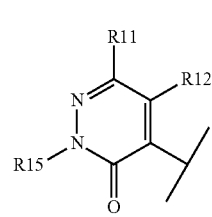

(ak) 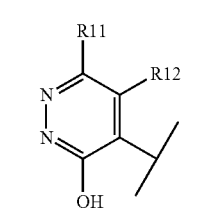

in which R7, R8, R9, R10, R11, R12, R13, R14 and R15 have the meaning given hereinafter, R5 represents a hydrogen atom, a fluorine atom, an alkyl radical having from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents an R16 radical, a halogen, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16, R7a represents a hydrogen atom or an alkyl radical having from 1 to 5 carbon atoms, R8 represents a hydrogen atom, a halogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently chosen from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 or —CO$_2$R16 radical, or alternatively, when two of the R9, R10, R11 and R12 radicals are in the ortho position on an aromatic or heteroaromatic ring selected from the group consisting of the rings corresponding to formulae (p) to (z) and (aa) to (ak) above, then they can together form, with the bond which links them together, an aryl, heteroaryl, cycloalkyl or heterocycloalkyl ring, R13 and R14 are identical or different and are independently chosen from the group consisting of a hydrogen atom, a halogen atom, and an alkyl, —CF$_3$, —OCF$_3$, —OH, —SH, —CN, —SO$_2$R16, —SO$_2$NR16R17, —NHSO$_2$NR16R17, —NR16R17, —NR16CONR16R17, —NR16COR17, —NR16CO$_2$R17, —CONR16R17, —COR16 or —CO$_2$R16 radical, R15 represents a hydrogen atom or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X and X', which may be identical or different, represent an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

2. The compound as claimed in claim 1, characterized in that, in the abovementioned formula (I):

R1 represents a hydrogen atom,
R2 represents a six-membered ring chosen from the structures (1), (5), (6) and (7) below:

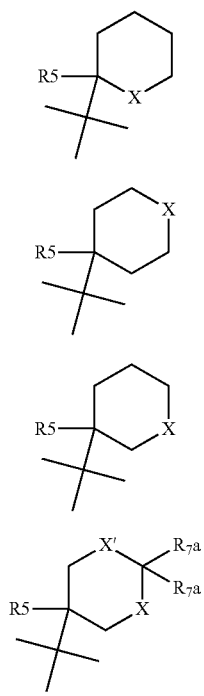

(1)

(5)

(6)

(7)

in which R5, X, X' and R7a have the meaning given hereinafter,
R3 represents an aromatic or heteroaromatic ring selected from the group consisting of the rings corresponding to formulae (a), (b) and (d) below:

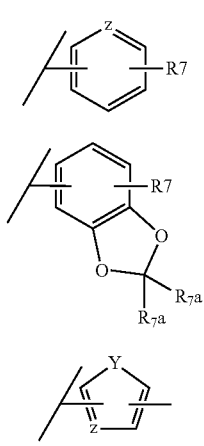

(a)

(b)

(d)

in which R7, R7a, Y and Z have the meaning given hereinafter, it being specified that the rings (a), (b) and (d) can optionally bear several R7 groups, which may be identical or different, the total number of such R7 groups being at most equal to the number of substitutable atoms of the ring;
R4 represents an aromatic or heteroaromatic ring selected from the group consisting of the rings corresponding to formulae (p), (q), (t), (z), (ad), (ag) and (ah) below:

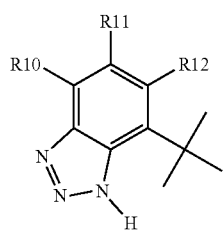

(p)

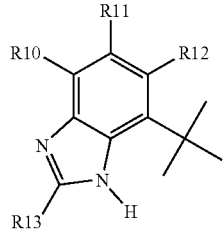

(q)

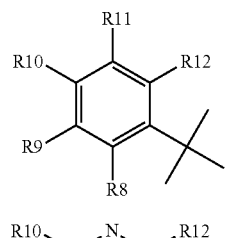

(t)

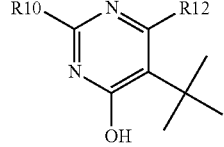

(z)

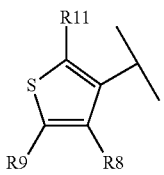

(ad)

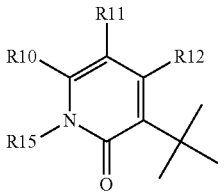

(ag)

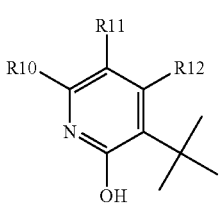

(ah)

in which R8, R9, R10, R11, R12, R13 and R15 have the meaning given hereinafter,
R5 represents a hydrogen atom, a fluorine atom, an alkyl radical comprising from 1 to 5 carbon atoms or a fluoroalkyl or perfluoroalkyl radical comprising from 1 to 5 carbon atoms,
R6 represents a hydrogen atom, a —COOtBu radical or a —COOBn radical, R7 represents an R16 radical, a halogen, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16, R7a represents a hydrogen atom or an alkyl radical containing from 1 to 5 carbon atoms, R8 represents a hydrogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently chosen from the group consisting of a hydrogen atom, a halogen atom and an alkyl, alkoxy, —CF$_3$, —OCF$_3$, —OH, —NO$_2$, —CN, —SO$_2$R16, —SO$_2$NR16R17, —NR16COR17, —NR16CO$_2$R17, —CONR16R17, —COR16 or —CO$_2$R16 radical, or alternatively, when two of the R9, R10, R11 and R12 radicals are in the ortho position on an aromatic or heteroaromatic ring selected from the group consisting of the rings corresponding to formulae (p), (q), (t), (z), (ad), (ag) and (ah) above, then they can together form, with the bond which links them together, an aryl, heteroaryl, cycloalkyl or heterocycloalkyl ring, R13 is chosen from the group consisting of a hydrogen atom, a halogen atom, and an alkyl, —CF$_3$, —OCF$_3$, —OH, —SH, —CN, —SO$_2$R16, —SO$_2$NR16R17, —NHSO$_2$NR16R17, —NR16R17, —NR16CONR16R17, —NR16COR17, —NR16CO$_2$R17, —CONR16R17, —COR16 or —CO$_2$R16 radical, R15 represents a hydrogen atom or an —OH, —SO$_2$R16, —COR16, —CO$_2$R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH$_2$COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X and X', which may be identical or different, represent an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

3. The compound as claimed in claim 1 or 2, characterized in that, in the abovementioned formula (I):

R1 represents a hydrogen atom,

R2 represents a six-membered ring chosen from the structures (5) and (6) below:

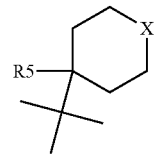

(5)

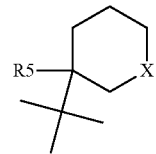

(6)

in which R5 and X have the meaning given hereinafter,

R3 represents a heteroaromatic ring corresponding to formula (d) below:

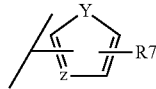

(d)

in which R7, Y and Z have the meaning given hereinafter, it being specified that the ring (d) can optionally bear several R7 groups, which may be identical or different, the total number of such R7 groups being at most equal to the number of substitutable atoms of the ring;

R4 represents an aromatic ring corresponding to formula (t) below:

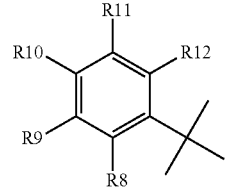

(t)

in which R8, R9, R10, R11 and R12 have the meaning given hereinafter,

R5 represents a hydrogen atom, a fluorine atom, an alkyl radical comprising from 1 to 5 carbon atoms or a fluoroalkyl or perfluoroalkyl radical comprising from 1 to 5 carbon atoms, R6 represents a hydrogen atom, a —COOtBu radical or a —COOBn radical, R7 represents a halogen atom, or an R16, —CF$_3$, —COR16, —OR16, —NR16R17, —NO$_2$, —CN, —SO$_2$R16, —SO$_2$NR16R17, —NR16COR17, —CONR16R17, —NR16CO$_2$R17 or —CO$_2$R16 radical, R8 represents a hydrogen atom, or an —OH, —SH, —CONHOR16, —CONR16OH, —NR16R17, —SO$_3$H, —OCOR16, —NHSO$_2$R16, —SO$_2$NR16R17, —NHCOR16, —CONR16R17, —NR16CO$_2$R17, —NHSO$_2$NR16R17, —CO$_2$R16, pyrrolyl, imidazolyl, triazolyl or tetrazolyl radical, R9, R10, R11 and R12 are identical or different and are independently chosen from the group consisting of a hydrogen atom, a halogen atom and an alkyl, alkoxy, —CF₃, —OCF₃, —OH, —NO₂, —CN, —SO₂R16, —SO₂NR16R17, —NR16COR17, —NR16CO₂R17, —CONR16R17, —COR16 or —CO₂R16 radical, or alternatively, when two of the R9, R10, R11 and R12 radicals are in the ortho position on an aromatic or heteroaromatic ring selected from the group consisting of the rings corresponding to formulae (p), (q), (t), (z), (ad), (ag) and (ah) above, they can together form, with the bond which links them together, an aryl, heteroaryl, cycloalkyl or heterocycloalkyl ring, R15 represents a hydrogen atom or an —OH, —SO₂R16, —COR16, —CO₂R16, aryl, heteroaryl, arylalkyl, heteroarylalkyl, alkyl, cycloalkyl or cycloalkylalkyl radical, R16 and R17 are identical or different and are independently chosen from the group consisting of a hydrogen atom, one of the following radicals: aryl, heteroaryl, arylalkyl, heteroarylalkyl, alkyl, fluoroalkyl having from 1 to 5 carbon atoms, cycloalkyl or cycloalkylalkyl, and a —CH₂COOR18 group in which R18 represents an alkyl radical having from 1 to 5 carbon atoms, or alternatively, when R16 and R17 are borne by the same nitrogen atom, they form a heterocycle having between 3 and 7 ring members and optionally comprising one or two heteroatoms chosen from oxygen, sulfur and nitrogen in addition to the common nitrogen atom by which they are borne, it being possible for said heterocycle to be substituted with an alkyl group having from 1 to 5 carbon atoms or a —COOR18 group in which R18 represents an alkyl radical having from 1 to 5 carbon atoms;

X represents an oxygen atom, a sulfur atom, or a nitrogen atom substituted with an R6 radical, Y represents an oxygen atom, a sulfur atom, or a nitrogen atom substituted with an R15 radical, and Z represents a carbon or nitrogen atom.

4. A pharmaceutical composition comprising an effective amount of a compound, or of a pharmaceutically acceptable salt of said compound, as claimed in claim 1, in combination with a pharmaceutically acceptable solvent or support.

5. The compound as claimed in claim 1 or the pharmaceutical composition as claimed in claim 4, for use as a medicament.

6. The compound as claimed in claim 1, chosen from the list consisting of:
1/ 2-hydroxy-N,N-dimethyl-3-(2-{[(5-methylfuran-2-yl)-(tetrahydropyran-4-yl)methyl]amino}-3,4-dioxocyclobut-1-enylamino)benzamide
2/ 2-hydroxy-N,N-dimethyl-3-(2-{[(5-methylfuran-2-yl)-(tetrahydrothiopyran-4-yl)methyl]amino}-3,4-dioxocyclobut-1-enylamino)benzamide
3/ tert-butyl 4-[[2-(3-dimethylcarbamoyl-2-hydroxyphenylamino)-3,4-dioxocyclobut-1-enylamino]-(5-methylfuran-2-yl)methyl]piperidine-1-carboxylate
4/ benzyl 4-[[2-(3-dimethylcarbamoyl-2-hydroxyphenylamino)-3,4-dioxocyclobut-1-enylamino]-(5-methylfuran-2-yl)methyl]piperidine-1-carboxylate
5/ tert-butyl 3-[[2-(3-dimethylcarbamoyl-2-hydroxyphenylamino)-3,4-dioxocyclobut-1-enylamino]-(5-methylfuran-2-yl)methyl]piperidine-1-carboxylate
6/ 2-hydroxy-N,N-dimethyl-3-(2-{[(5-methylfuran-2-yl)-(4-methyltetrahydropyran-4-yl)methyl]amino}-3,4-dioxocyclobut-1-enylamino)benzamide.

\* \* \* \* \*